(12) United States Patent
Lachapelle

(10) Patent No.: US 6,290,498 B1
(45) Date of Patent: Sep. 18, 2001

(54) WATER VALVE FOR DENTAL HANDPIECE

(76) Inventor: Claude Lachapelle, 170, bld. Paquette, Mont-Laurier, (Quebec) (CA), J9L 1J5

( * ) Notice: Subject to any disclaimer, the term of this patent is extended or adjusted under 35 U.S.C. 154(b) by 0 days.

(21) Appl. No.: 09/373,743

(22) Filed: Aug. 13, 1999

Related U.S. Application Data

(60) Provisional application No. 60/096,720, filed on Aug. 17, 1998.

(51) Int. Cl.$^7$ .............................. A61C 1/10; A61C 1/12; A61C 17/02
(52) U.S. Cl. ................................. 433/84; 433/80
(58) Field of Search .................. 433/80, 84, 85, 433/88, 98, 100, 28

(56) References Cited

U.S. PATENT DOCUMENTS

| | | | |
|---|---|---|---|
| 2,274,893 | * | 3/1942 | Freedman . |
| 3,673,709 | * | 7/1972 | Page ........................................ 433/84 |
| 3,838,516 | * | 10/1974 | Borochaner ......................... 433/84 X |
| 3,961,640 | * | 6/1976 | Baker ................................. 433/98 X |
| 5,044,952 | * | 9/1991 | Castellini ........................... 433/98 X |
| 5,201,654 | * | 4/1993 | Kuehn et al. . |

FOREIGN PATENT DOCUMENTS

| | | |
|---|---|---|
| 89 07 473 U | 8/1989 | (DE) . |
| 1 424 715 | 2/1976 | (GB) . |

OTHER PUBLICATIONS

Publication—Dental Unit Waterlines; Rella P. Christensen, Jan. 1998.*
Microbiologie des conduites d'eau dentaires: plus qu'une histoire d'eau. Jean Barbeau, Nov. 1997.*
Equipement Dentech Advance—Servident, Apr./May/Jun. 1999.*
Publication—Dental Unit Waterlines; Rella P.Christensen, Jan. 1998.
Microbiologie des conduites d'eau dentaires: plus qu'une histoi d'eau. Jean Barbeau, Nov. 1997.

* cited by examiner

Primary Examiner—Nicholas D. Lucchesi
(74) Attorney, Agent, or Firm—F. Martineau

(57) ABSTRACT

The water valve links a dental handpiece to its tubing. The tubing conventionally has a high-pressure air tube in which air will flow when the handpiece is selectively activated, a cooling water tube for cooling the handpiece head and the patient's tooth during use of the handpiece head, a cooling air tube for converting the cooling water flow into an atomized water spray, and a discharge tube, in which part of the high-pressure air flow are carried away from the dental handpiece. The water circulation device includes a valve which has four inner conduits each operatively linking the respective tubes to the dental handpiece. Furthermore, a bypass channel is formed in the valve, between the valve member water conduit and discharge conduit. A piston is movable in the bypass channel, between a first unobstructive position in which the water is free to flow from the water conduit into the discharge conduit, and a second obstructive position in which the piston blocks in a fluid-tight fashion the bypass channel, to prevent the water from flowing into the discharge conduit. A spring continuously forces the piston towards its first unobstructive position. Thus, in the handpiece inoperative condition, when no high-pressure air flow runs through the high-pressure air conduit, the water is free to flow in the valve from the water conduit into the discharge channel, thus not reaching the handpiece and continuously flowing to prevent the water from stagnating. When the handpiece is activated, the high-pressure air flow forces the piston through an air channel communicating with the piston channel, against the action of the spring towards its second limit position, thus blocking the bypass channel and allowing the water to flow conventionally into the handpiece.

13 Claims, 4 Drawing Sheets

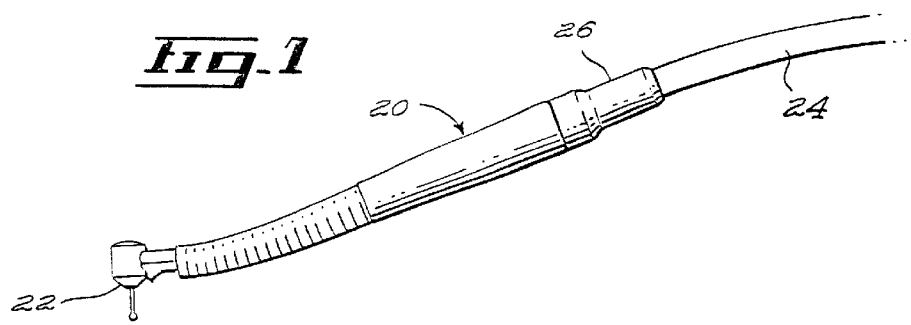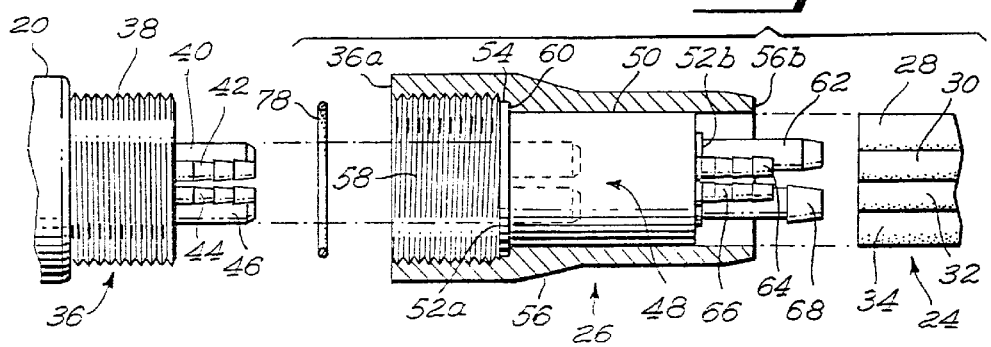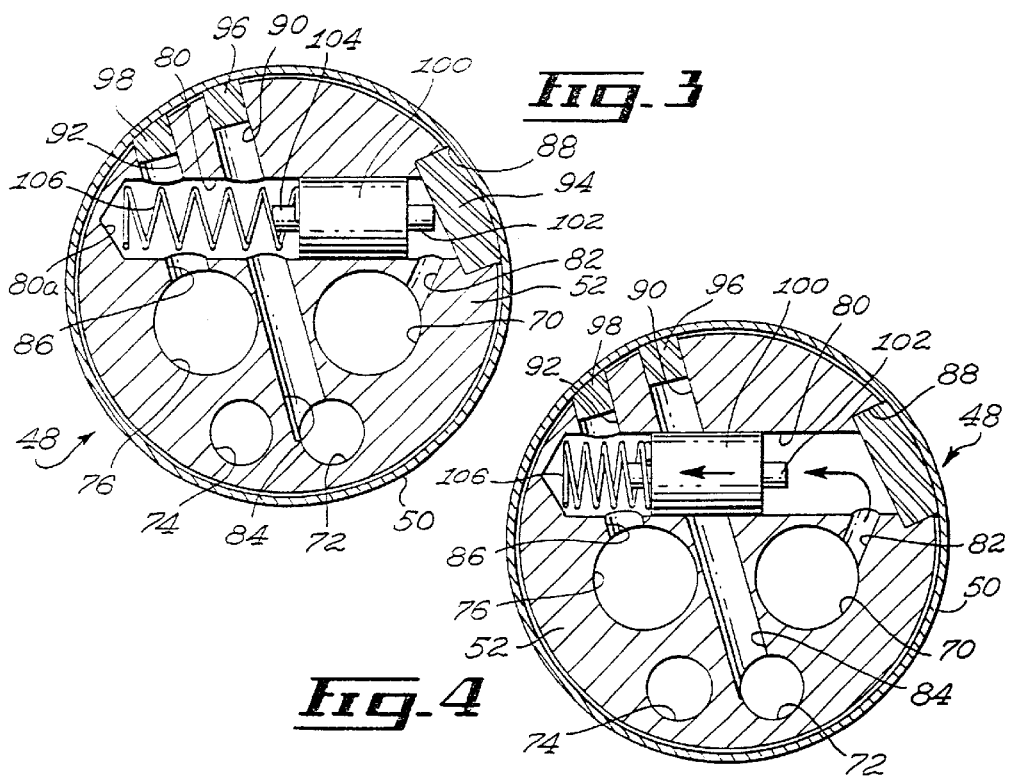

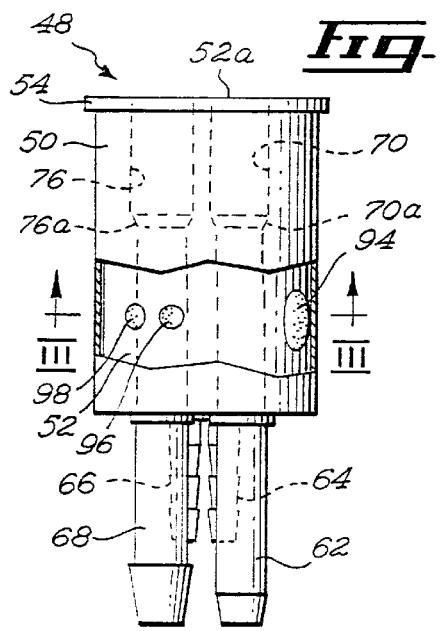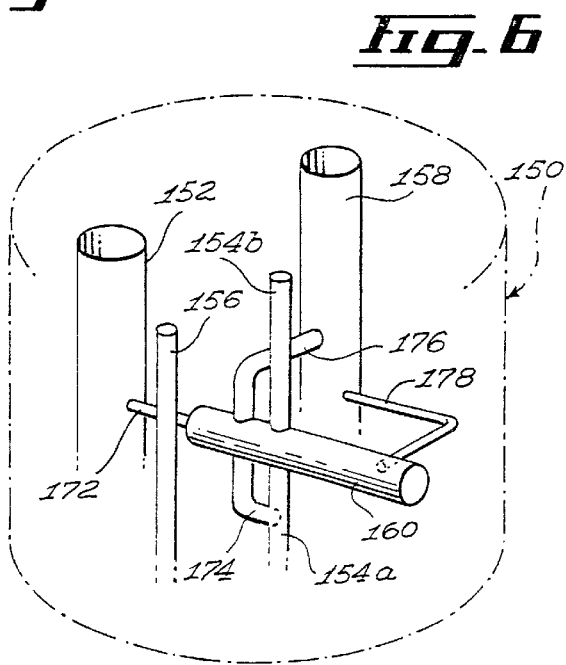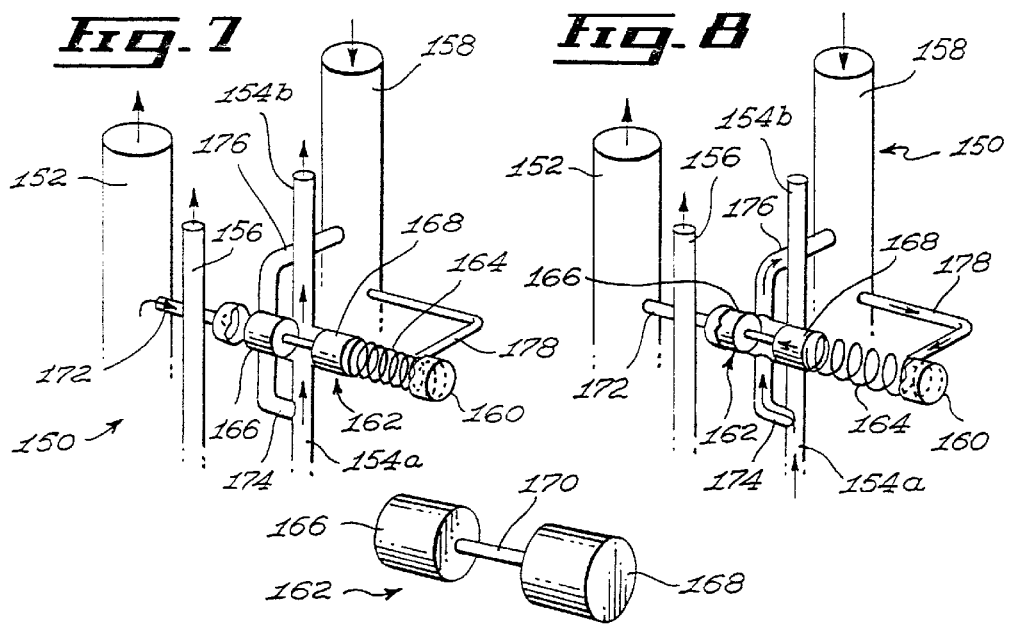

US 6,290,498 B1

WATER VALVE FOR DENTAL HANDPIECE

CROSS REFERENCE DATA

Co-pending provisional U.S. patent application Ser. No. 60/096,720 filed Aug. 17 1998 is hereby incorporated by way of reference into the present patent application.

FIELD OF THE INVENTION

The present invention relates to dental handpieces and more particularly to a constant water flow device or valve for a handpiece of a dental unit waterline.

BACKGROUND OF THE INVENTION

Dental handpieces, e.g. equipped with a bur, are of common use in dental cabinets. The pneumatic bur, located at the distal free end portion of the handpiece, rotates at high speed under the propelling force of a primary air flow provided by an air turbine, for allowing efficient drilling operations to be performed in the patient's teeth. Cooling of the bur is necessary to prevent the bur and the tooth from becoming too hot under the high velocity friction forces induced therein. The cooling is achieved by means of an atomized water spray which is projected against the tooth and the bur drilling head. The propelling air flow is recovered and discharged. However, the cooling water droplets are expelled into the patient's mouth through the bur head.

An important problem associated with conventional bur units is that the cooling water often develops high counts of microorganisms, particularly anaerobic bacteria, due to water stagnation in the water conduits or tubes feeding, the handpiece. Use of this contaminated water can worsen mouth infections for the patients in the case of pathogenic bacteria colonies, and at least leave a bad taste in the patient's mouth. Quantitatively, the amount of water used by the dental handpiece during dental procedures is very small. Due to this low water flow rate and to the relatively important length of the water lines connected to the dentist's water providing apparatus, water therein is likely to stagnate for a few days, typically for one or two weeks on average, before it is expelled at the outlet for cooling the distal bur head. The medium of the water lines containing stagnating water is thus favourable to bacteria development, and the bacteria count may increase significantly during stagnation time at favourable dental room temperatures. This may result in local infections of a patient's oral cavity upon a portion of the high count bacteria water being expelled into his mouth, especially if the patient has flesh wounds resulting either from the dentist's intervention or other causes.

Chemical compounds can be injected at regular time intervals into the dentist water line network to sterilize the water tubing and eliminate the bacteria formations in the water lines, when water lines are not in operation. However, these cleaning products are likely to—and often do—damage the valves and other parts of the water tubes, especially the rubber gaskets and valves therein, due to their chemical composition. Also, a patient may be contaminated by the often toxic cleaning products if residues of this chemical cleaner remain when the water tubes are not rinsed properly after the cleaning products have been circulated therein. Thus, particular efforts have to be undertaken to both cleanse and rinse the water tubes.

It is known to use sterilized water bags to supply sterile water for dental operations to be pursued without risk of bacterial infection from water tap pathogenic bacteria formations. However, this alternative is much more expensive than using the conventional tap water, and requires that the dentist or dental surgeon connects his dental unit apparatus to such a bag before use, and it is also prone to promoting bacterial formation due to water stagnation in the tubing linking the water bag to the dental handpiece.

U.S. Pat. No. 2,274,893 issued in 1942 to H. Freedman discloses a dental apparatus for feeding a water spray into the mouth of a person. The Freedman apparatus includes a water tube which is equipped at its intermediate portion with a drainage pipe provided with a flap valve. The tube intermediate portion is destined to be positioned lower than the tube proximal inlet and distal outlet extremities, so that gravity forces the water in the pipe down towards the drainage pipe to evacuate same. The flap valve includes a resilient flap which remains opened in an unbiased condition, thus allowing the water to freely flow out into the drainage pipe; and which closes under the pressure differential to block the drainage pipe upon water flowing from the inlet extremity to the outlet extremity. Thus, water back-flow from the distal ejector nozzle into the water tube is allegedly controlled.

A problem with the dental apparatus disclosed in the Freedman apparatus, is that it requires the water tube to be positioned in a particular way, i.e. with its intermediate portion located lower than the remaining segments of the tube. If other segments are lowered under the level of the drainage pipe, then water stagnation is likely to occur. Also, the dental apparatus of the Freedman apparatus is especially adapted for a water spray nozzle of old construction, where the water flow rate is greater than in modern dental handpieces; thus, the purpose of the drainage pipe in the Freedman patent is to prevent water from running back from the outlet nozzle into the tube, and eventually into the water reservoir. It is not adapted to prevent water stagnation, and does not offer any form of continuous water flow in the tube.

OBJECT OF THE INVENTION

It is the object of the present invention to provide a water circulation valve for a dentist cabinet, which allows constant water flow in the dentist's handpiece water lines even when the dentist cabinet is not in use, to help prevent microorganism deposition and accumulation therein.

SUMMARY OF THE INVENTION

The present invention relates to a valve member for operatively linking a dentist cabinet dental handpiece of the type which selectively requires a water flow and which includes a water inlet nozzle and a discharge outlet nozzle, to a main tubing of the type having a water tube outlet and a discharge tube inlet, the water tube outlet providing a continuous positive water flow, said valve member comprising:

a water conduit for operatively fluidingly linking the water tube outlet to the dental handpiece water inlet nozzle, a continuous positive water pressure thus being present in said water conduit for allowing selective water flow out through the dental handpiece;

a discharge conduit for operatively fluidingly linking the discharge tube inlet to the dental handpiece discharge outlet nozzle, the pressure in said discharge conduit being, inferior to the pressure in said water conduit;

a bypass channel linking said water conduit to said discharge conduit; and an actuator, selectively movable in said bypass channel between a first limit position in which said actuator allows fluid access through said bypass channel from said water conduit to said discharge conduit, and a second limit position in which said actuator blocks in a fluid-tight fashion said bypass channel for preventing fluid from flowing between said water conduit and said discharge conduit:

wherein in said first limit position of said actuator, water flowing in said water conduit will be redirected through said bypass channel to be dispatched in said discharge conduit for allowing continuous flow of the water in the tubing to prevent water stagnation, while in said second limit position of said actuator, water flowing in said water conduit will be forced to flow through said valve member and into the dental handpiece.

Preferably, the dental handpiece further is of the type having a high-pressure air inlet nozzle and the tubing further is of the type having a high-pressure air tube outlet selectively providing a high-pressure air flow, said valve member further comprising:

a biasing member, for continuously biasing said actuator towards said first limit position;

a high-pressure air conduit for operatively fluidingly linking the high-pressure air tube outlet to the dental handpiece water inlet nozzle; and an air channel linking said air conduit to said bypass channel, for forcibly biasing said actuator towards said second position, against the action of said biasing member, upon the high-pressure air flow being fed into said high-pressure air conduit; said actuator, in all positions thereof, sealingly blocking said bypass channel to prevent fluid from flowing between said air conduit and both said water conduit and said discharge conduit.

Preferably, said actuator is a piston slidable in said bypass channel.

Preferably, said biasing member is a coil spring located in said bypass channel.

The invention further relates to the valve member as described hereinabove, in combination with the dental handpiece, said dental handpiece having a head portion requiring in an operative condition thereof a high-pressure air flow fed by a handpiece high-pressure air conduit connected to said air inlet nozzle, and a cooling water flow fed by a handpiece cooling water conduit connected to said water inlet nozzle, said dental handpiece expelling at least a portion of said air and water flows through a handpiece discharge conduit connected to the handpiece discharge outlet nozzle.

The invention also relates to a water circulation device for preventing water stagnation in the tubing of a dentist cabinet dental waterline unit, said water circulation device for linking a dental handpiece to the tubing, the tubing of the type having a high-pressure air tube for selectively providing a high-pressure air flow to the dental handpiece, a cooling water tube for providing a continuous water cooling water flow for the dental handpiece, a cooling air tube for providing a cooling air flow for atomizing the cooling water into a cooling water spray, and a discharge tube, in which part of the cooling water spray and part of the high-pressure air flow are carried away from the dental handpiece, said water circulation device including a valve member comprising:

a high-pressure air conduit, a cooling air conduit, a cooling water conduit and a discharge conduit, each for operatively fluidingly linking respectively the high-pressure air tube, the cooling water tube, the cooling air tube and the discharge tube to the dental handpiece;

a bypass channel fluidingly linking said cooling water conduit to said discharge conduit;

a piston movable in said bypass channel, between a first unobstructive position in which the water is free to flow from the water conduit into the discharge conduit, and a second obstructive position in which said piston blocks in a fluid-tight fashion said bypass channel, to prevent the water from flowing into the discharge conduit;

a biasing member continuously biasing said piston towards said first limit position; and an air channel linking said bypass channel to said high-pressure air conduit, with said piston blocking said bypass channel between said air channel and both said water and said discharge conduits in all positions of said piston, said piston being forcibly moved towards said second limit position responsive to the presence of a high-pressure air flow in said high-pressure air conduit;

wherein, when no high-pressure air flow runs through said high-pressure air conduit, said piston remains in said first limit position under the bias of said biasing member and water is free to flow through said bypass channel from said water conduit into said discharge conduit, thus not reaching the handpiece, for allowing the water to continuously flow to prevent the water from stagnating in the tubing; and wherein, when a high-pressure air flow runs through said high-pressure air conduit, the high-pressure air flow forces said piston against the action of said biasing member towards said second limit position, thus blocking said bypass channel and allowing the water to flow out of said cooling water conduit for feeding the handpiece.

Preferably, said actuator is a piston slidable in said bypass channel.

Preferably, said bypass channel comprises a piston channel segment, in which said piston is slidable between said first and second limit positions, a water channel segment linking said water conduit to said piston channel segment, and a discharge channel segment linking said discharge conduit to said piston channel segment, with said water channel segment being located intermediate said discharge channel segment and said air channel, with said piston being located in said first limit position intermediate said air channel and said water and discharge channel segment, and with said piston blocking said water channel segment in said second limit position.

Preferably, at least one channel among said piston channel segment, said water channel segment, said discharge channel segment and said air channel is pierced from the outer periphery of said valve member inwardly therein thus forming at least one corresponding channel segment opening at the periphery of said valve member, said at least one channel segment opening being blocked with a sealing plug.

Preferably, the water circulation device comprises a sealing ring located around said valve member and holding each said at least one channel segment opening.

Preferably, said biasing member is a coil spring located in said piston channel segment.

Preferably, the water circulation device further comprises a hollow connector sleeve carrying said sleeve member, said connector sleeve having a first end portion for complementary engagement to said dental handpiece, and a second end portion for complementary engagement to said tubing.

The invention also relates to a process of making a water circulation device as defined hereinabove, comprising the steps of:

a) moulding a valve member blank;

b) longitudinally piercing in said valve member blank said high-pressure air conduit, said cooling water conduit, said cooling air conduit and said discharge conduit;

c) transversely piercing in said valve member blank said air piston channel segment, said air channel, said water channel segment and said discharge channel segment, thus creating at least one transverse opening in said blank;

d) installing sealing plugs in each one of said at least one openings; and e) forcing in a friction-fit engagement said sealing ring about said valve member for holding said plugs.

DESCRIPTION OF THE DRAWINGS

In the annexed drawings:

FIG. 1 is a side elevation of a dental handpiece equipped with a bur at its distal end, together with a portion of the water and air tubes which are connected to the handpiece by means of a water circulation device according to the invention;

FIG. 2 is an exploded side elevation, at an enlarged scale, of the proximal end of the dental handpiece, together with the water circulation device according to a preferred embodiment of the invention and with the distal end portion of the water and air tubes, the outer connector sleeve of the water circulation device being shown in cross-section for allowing the inner valve member to be shown, and two of the four inner conduits of the valve member being partly shown in dotted lines;

FIG. 3 is an enlarged cross-sectional view taken along line Ill—Ill of FIG. 5, with the piston of the valve member being shown in a first limit position;

FIG. 4 is a view similar to FIG. 3, but with the piston being in a second limit position;

FIG. 5 is an elevational view of the water valve member according to the invention, with a portion of the sealing ring being broken for showing the sealing plugs of the valve member main body;

FIG. 6 is a schematic perspective view of the inline fluid circuit of an alternate embodiment of the water valve member of the invention. suggesting in phantom lines the outer limits of the valve member main body, FIGS. 7 and 8 are views similar to FIG. 6, but being partially broken to show the interior of the valve member piston channel, with the piston being shown in its second and first limit positions respectively in FIGS. 7 and 8;

FIG. 9 is a perspective view of the piston of the valve member of the embodiment of FIGS. 6 to 8.

DETAILED DESCRIPTION OF THE EMBODIMENTS

Figure 10:
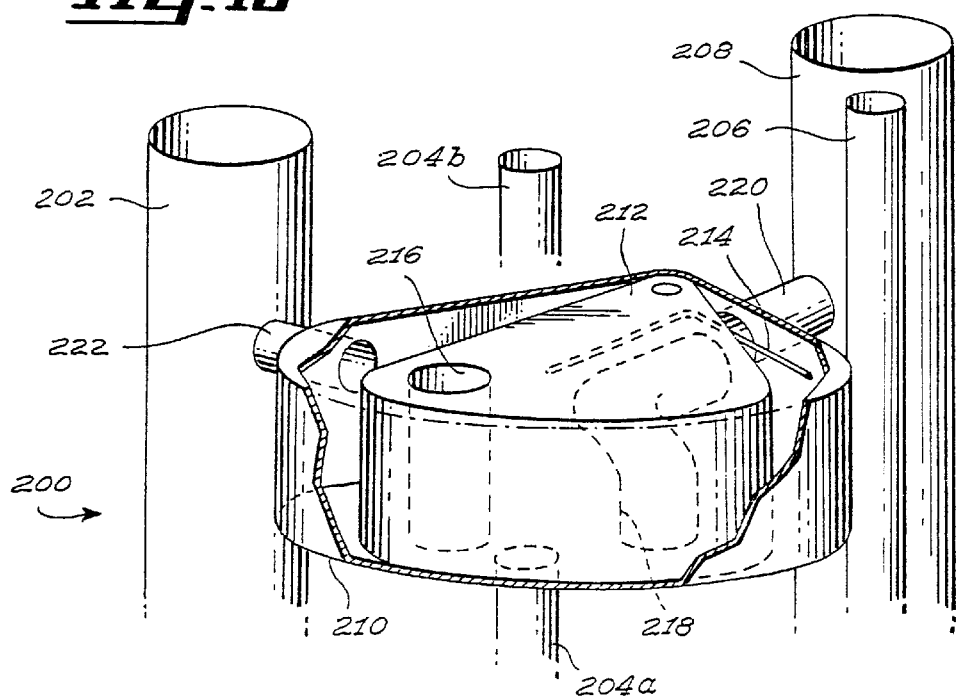
FIGS. 10, 11, 12 and 13 are schematic perspective views of respective third, fourth, fifth and sixth embodiments of water valve members of the invention.

FIG. 1 shows a conventional rigid dental handpiece 20, equipped with a conventional bur head 22. An elongated flexible main tube 24 is connected at one end to handpiece 20 through the instrumentality of a water circulation device 26 according to the invention, as will be detailed hereinafter. Main tube 24 is connected to a tap water source atits other end opposite handpiece 20, and as shown in FIG. 2. comprises four tubes tangentially attached to one another, namely:

a high pressure air tube 28, e.g. for providing a driving air flow for pneumatically rotating the bur;

a cooling water tube 30, for feeding cooling water from the main water tap system to the bur head, for cooling the bur rotating at high velocity and for cooling the tooth being drilled by the bur;

a cooling air tube 32, for providing an air flow for atomizing the cooling water from tube 30 at the bur head 22 into a cooling water spray; and a discharge tube 34 for discharging the high-pressure air flow after it has run through the bur head to rotate the bur, and for discharging part of the atomized cooling water spray.

As known in the art, other tubes can be linked to the flexible elongated main tube 24, such as power cable-carrying tubes for lighting purposes or the like.

FIG. 2 further shows that the conventional dental handpiece 20 is provided, opposite its distal bur head 22, with a proximal end portion 36 having a thread 38 from which protrudes four nozzles, namely a high-pressure air inlet nozzle 40, a cooling water inlet nozzle 42, a cooling air inlet nozzle 44 and a discharge outlet nozzle 46, each for being connected to the respective tubes 28, 30, 32 and 34 of main tube 24, through the instrumentality of a water circulation device 26 according to the invention, as will be detailed hereinafter. The handpiece nozzles 40, 42, 44, 46 are co-extensive with and connected to inner handpiece conduits (not shown) which carry the respective fluids to or from the bur head portion 22, as known in the art.

FIGS. 2 to 5 show that the water circulation device 26 according to the invention comprises a water valve member 48 (shown separately in FIG. 5) having an outer sealing ring 50 enclosing a cylindrical inner main body 52 made of a suitable corrosion-resistant material, e.g. brass or stainless steel, or even a suitable plastic material. The valve member main body 52 has a first distal end 52a, which defines a peripheral radially-projecting flange 54. and a second proximal end 52b opposite its first end 52a. As shown in FIG. 2, valve member 48 is inserted inside a connector sleeve 56 which defines a first opened distal end portion 56a having an inner thread 58, and a second opposite opened proximal end portion 56b opposite its first end portion 56a. Furthermore, a peripheral shoulder 60 is located longitudinally inwardly of thread 58, and is sized to receive in stable abutment the peripheral flange 54 of valve member 48 when the latter is coaxially inserted into sleeve connector 56 as shown in FIG. 2. Valve member nozzles are provided at the proximal end 52b of the valve member main body 52, namely a high-pressure bur air nozzle 62, a cooling water nozzle 64, a cooling air nozzle 66 and a discharge nozzle 68, all for respective friction-fit connection into the slightly resilient tubes 28, 30, 32 and 34 of main tube 24.

FIGS. 3 to 5 further show that the valve member main body 52 is fall, and longitudinally pierced with a high-pressure bur air conduit 70, a cooling water conduit 72, a cooling air conduit 74 and a discharge conduit 76, which are all coextensive with and connected to the respective valve member nozzles 62, 64, 66 and 68, and which are all opened at the valve member main body distal end 52a for allowing the respective dental handpiece nozzles 40, 42, 44 and 46 to engage conduits 70, 72, 74 and 76 respectively. Thus, when the valve member 48 is operatively inserted inside sleeve connector 56 as shown in FIG. 2 and as described hereinabove, the thread 38 of handpiece 20 can engage the complementary thread 58 of sleeve member 56, with the handpiece nozzles 40, 42, 44 and 46 each being fluidingly connected to a respective valve member conduit 70, 72, 74 and 76. However, it must be noted that nozzles 40, 42, 44 and 46 extend well short of the valve member proximal end 52b, and more particularly extend down to an intermediate tapered portion 70a, 76a of conduits 70, 72, 74, 76 shown in dotted lines in FIG. 5 (with the conduits 72, 74 not being shown in FIG. 5). An annular seal 78, e.g. made of rubber, is preferably inserted between the handpiece proximal end portion 36 and the valve member distal end 52a.

Four transverse channels 80, 82, 84, 86 are made in the valve member main body 52, at an intermediate portion thereof, and are more particularly located spacedly between the valve member main body proximal end 52b and the free extremities of the handpiece nozzles 40, 42, 44, 46 when the latter are operatively inserted into valve member 48. The four transverse channels are a cylindrical piston channel 80 extending spacedly adjacent to the bur air conduit 70 and discharge conduit 76; a first inner air channel 82 fluidingly interconnecting the bur air conduit 70 to piston channel 80; a second inner water channel 84 fluidingly interconnecting the cooling water conduit 72 to the piston channel 80; and a third inner discharge channel 86 fluidingly interconnecting the discharge conduit 76 to the piston channel 80. As shown in the drawings, second inner channel 84 is located between the first and the third inner channels 82, and 86, and is substantially parallel thereto.

To facilitate the production of valve member 48, and as shown in FIGS. 3–5, transverse channels 80, 82, 84, 86 are made by piercing the valve member main body 52 inwardly from its peripheral surface, with the four channels not extending all the way through main body 52. Thus, a first channel opening 88 is created by piercing the piston channel 80 and the first inner channel 82; a second opening 90 is created by piercing the second inner channel 84; and a third channel opening 92 is created by piercing the third inner channel 86. It is understood that channel openings 88, 90, 92 serve no purpose per se, since they owe their existence merely to the through-piercing of the transverse channels 80, 82, 84, 86. Suitable first, second and third sealing plugs 94, 96, 98, e.g. made of rubber, respectively seal the first, second and third channel openings 88, 90, 92. The sleeve member sealing ring 50 is inserted coaxially about the valve member main body 52 until it axially abuts against the valve member main body flange 54, sealing ring 50 frictionally engaging the sealing plugs 88, 90, 92 which prevent sealing ring 50 from accidentally sliding off from main body 52, while sealing ring 50 prevents sealing plugs 88, 90, 92 from being accidentally expelled from their respective channel openings 88, 90, 92.

A cylindrical piston 100, e.g. made of nylon, is slidable inside cylindrical piston channel 80, with piston 100 being sized to sealingly fit inside piston chamber 80. Piston 100 is provided with a pair of coaxial integral studs 102, 104 at both of its extremities, the diameter of studs 102, 104 being inferior to the diameter of piston 100. A coil spring 106 coaxially located in piston chamber 80, is installed between the piston channel end wall 80a and the piston 100, preferably being wound partially around stud 104 for enhanced stability of the spring and piston engagement. Coil spring 106 continuously biases piston 100 towards the first channel opening 88.

In use, when handpiece 20 is in an inoperative condition, there is no pressure in the bur air conduit 70 and piston 100 is biased by coil spring, 106 towards a first limit position, shown in FIG. 3, in which stud 102 abuts against first sealing plug 94. In this position, the piston 100 main body is located between the first and the second inner channels 82, 84, without blocking any of these two channels. The cooling water under pressure in water conduit 72 since it cannot be expelled at the bur head 22 while the latter is inoperative in reoriented, in this first position of piston 100, to flow through second inner channel 84, into piston chamber 80, and out into discharge conduit 76 through the third inner channel 86. Indeed, since no water output is possible at the bur head 22 when handpiece 20 is in its inoperative condition, the pressure differential between the communicating water conduit 72 and discharge conduit 76 will force the water to flow out into the discharge conduit 76, to be discarded.

When handpiece 20 is in an operative condition, i.e. that the bur head portion 22 is being rotated at high speed, a high-pressure air flow runs through the bur air conduit 70 and communicates with piston channel 80 through first inner channel 82. This high-pressure air flow biases piston 100 against the action of spring 106, towards a second limit position shown in FIG. 4. In this second position of piston 100, the main body of piston 100 blocks the opening of the second inner water channel 84 to the piston channel 80, thus effectively preventing the water from flowing from water cooling conduit 72 to discharge conduit 76. Consequently, the water flowing in water cooling conduit 72 may flow to the handpiece and to the bur head, for accomplishing its cooling purpose by being atomized by the air flowing in the cooling air conduit 74.

With the valve member 48 of the invention, water stagnation in the water tubes of the dental handpiece is completely obviated, which significantly hampers the microorganisms (in particular, bacteria) deposition and accumulation therein. Indeed, when the bur head 22, or more generally the dental handpiece 20, is not being used, the water continuously flows to be expelled through the discharge conduit and out into the local sewer outlet. This continuous water flow prevents the water from stagnating, and thus the water tubes become much less proper as a bacteria reproduction medium, since constantly flowing tap water is itself chemically treated with bactericidal agents, there is constant decontamination of the main tubing 24 and of the handpiece 20. It is understood that the water flow rate through the cooling water tube is very small, and thus no important water waste occurs due to the continuous water flow into discharge conduit 76.

One particular advantage of the valve member of the invention, is that it can be installed in a retro-fit fashion on existing tubing. Indeed, the conventional sockets provided on dental handpiece tubing are similar to the water circulation device of the present invention, to the exception that no water redirection occurs, since no transverse channels are provided therein. The conventional sockets are simply installed on the tubing outlets to allow easy installation and removal of dental handpieces, to be replaced by other handpieces. With the valve member of the present invention, the conventional socket may be replaced by the water circulation device 26, which will also act as a socket for receiving the dental handpiece and connecting same to the tubing due to sleeve connector 56. Thus, for the dental practitioner, little or no difference can be noticed between the conventional handpiece socket and the water circulation device of the invention.

FIGS. 6–13 show alternate embodiments of the invention. For the purpose of simplifying the drawings, the inline fluid conduits have been schematically shown as pipes, although it is understood that the preferred way to carry out the invention is to provide a full valve member body in which are pierced through-channels or conduits, due to manufacturing costs considerations of the valve member of such small dimension.

FIGS. 6–8 schematically show a second embodiment of a valve member 150 according to the invention, through which extend a high-pressure bur air conduit 152, a cooling water conduit 154, a cooling air conduit 156 and a discharge conduit 158, as with the first embodiment of the invention. A piston channel 160 transversely extends inside the main body of valve member 150, in which a piston 162 is slidable and continuously biased towards a first limit position, shown in FIG. 8, by a coil spring 164. As shown in FIG. 9, piston 162 comprises a first and a second spaced-apart cylinders 166, 168 integrally axially linked by a short spacer rod 170. FIGS. 6–8 further show that the cooling water conduit is separated into two segments 154a and 154b located respectively downstream and upstream of piston channel 160, and both open into an intermediate portion of piston channel 160 in fluid connection therewith and in facing register with each other.

Valve member 150 comprises a first inner air channel 172 which links the high-pressure bur air conduit to a first extremity of piston channel 160; a second inner bypass channel 174 which links cooling water conduit 154 to an intermediate portion of piston channel 160; a third inner bypass channel 176 which links discharge conduit 158 to an intermediate portion of piston channel 160, in register with second inner channel 174; and a fourth inner channel 178, which links discharge conduit 158 to piston channel 160 at the second extremity thereof, opposite its first extremity.

When the dental handpiece is not being used by the dental practitioner, there is no air pressure in the bur air conduit 152, and piston 162 is biased by coil spring 164 towards its first limit position shown in FIG. 8. In this position, the two cylinders 166, 168 of piston 162 are located on one side and the other of the two registering second and third inner channels 174, 176, with the piston rod 170 registering with the second and third inner channels 174, 176. Second cylinder 168 is positioned in register with the cooling water conduit downstream and upstream segments 154a, 154b and blocks same to prevent water from flowing from one to the other. Thus, the water flowing in the cooling water conduit downstream segment 154a is redirected through second inner channel 174, passes into the piston channel 160 between the two piston cylinders 166, 168 and around the piston rod 170, and flows out through the third inner channel 176 to be expelled into the discharge conduit 158. Consequently, when the dental handpiece 20 is not in use, there is a continuous water flow in valve member 150, to prevent water stagnation and microorganism build-up in the dental handpiece 20 and main tube 24.

When the dental handpiece is being used, a high-pressure air flow runs through the bur air conduit 152, and passes through the first inner channel 172 to bias piston 162 towards the piston channel second extremity, against the action of coil spring 164. In this second position of piston 162, first cylinder 166 is located in register with the openings of second and third bypass channels 174, 176, to block same and consequently prevent access from one to the other through piston channel 160, while the piston second cylinder 168 frees the way between the cooling water conduit segments 154a, 154b to allow the cooling water to flow from one to the other. Thus, the water can be fed to the handpiece bur head 22, to be being atomized by the cooling air flow and accomplish its cooling purpose. The purpose of the fourth inner channel 178 is to allow air to be fed and evacuated between piston 162 and the piston channel 160 second extremity, during the translational movements of piston 162.

FIG. 10 schematically shows the inline fluid circuit of a third embodiment of a valve member 200 according to the invention. In this embodiment, the valve member 200 comprises a pivotable actuator 212 which is pivotable inside an arcuate inner chamber 210. Actuator 212 is full and comprises a first and a second inner passages 216, 218 therein.

The cooling water conduit is divided by chamber 210 into a downstream segment 204a and an upstream segment 204b. In use, a spring 214 biases actuator 212 into a first limit position in which the second inner passage 218 of actuator 212 comes in register with the downstream segment 204a of the cooling water conduit. In this position of actuator 212, the cooling water is redirected through the elbowed second passage 218 of actuator 212, into chamber 210, out through a first inner channel 220 and into the discharge conduit 208. Thus, the water can be continuously evacuated through discharge conduit 208 and continuous water flow is achieved, to prevent water stagnation. However, when the bur head of the handpiece is power-rotated, a high-pressure air flow runs through the bur air conduit 202, through second inner channel 222 and into chamber 210, to pivotally bias actuator 212 against the action of spring 214 into a second limit position, in which the actuator first passage 216 comes in register with both the downstream and upstream segments 204a, 204b of the cooling water conduit to allow the water to flow through first passage 216 and to the dental handpiece.

Figure 11:
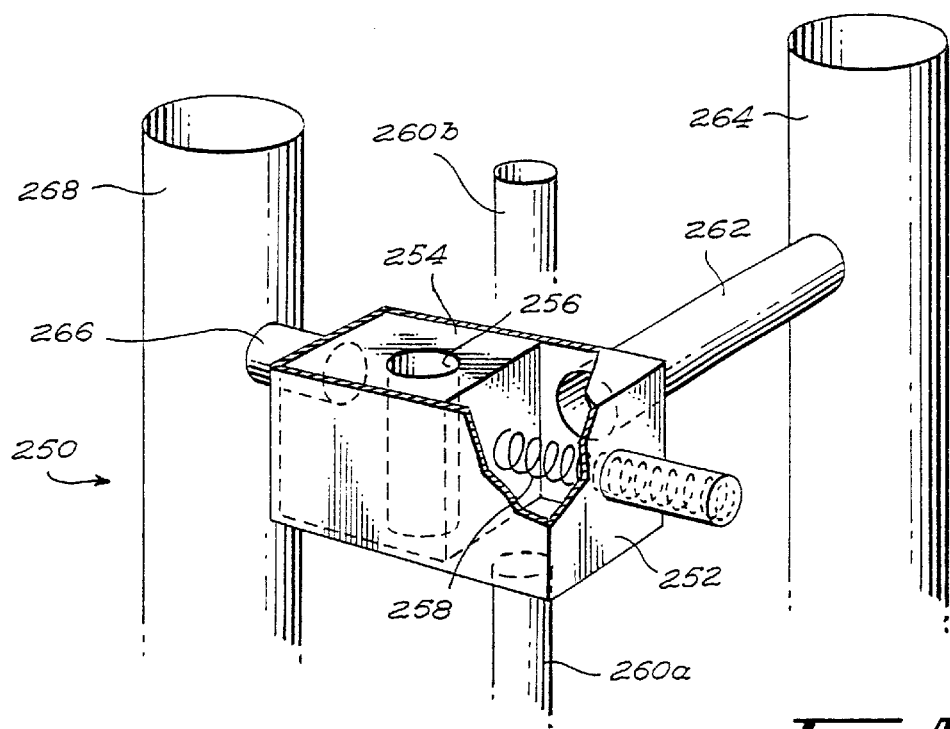

FIG. 11 schematically shows the inline fluid circuit of a fourth embodiment of a valve member 250 according to the invention. In this embodiment, the valve member 250 comprises an inner chamber 252 in which is slidable a block actuator 254 having a single passage 256 therein. In use, when the dental handpiece is in an inoperative condition, no air flow runs through the high-pressure air conduit 268, and block actuator 254 is biased by a coil spring 258 so that the downstream segment 260a of the cooling water conduit communicate through chamber 252 with a first transverse inner channel 262 which in turn is connected to the discharge conduit 264. Thus, in this position of block actuator 254, the water flows constantly through the water tubing, into the valve member to be dispatched through the discharge tube. When the bur head is activated, a high-pressure air flow enters chamber 252 through a second transverse inner channel 266 and from the bur air conduit 268, to bias block actuator 254 against the action of spring 258 until inner passage 256 comes in register with the downstream and upstream segments 260a, 260b of the cooling water conduit. Thus, the cooling water is allowed to be fed to the dental handpiece.

Figure 12:
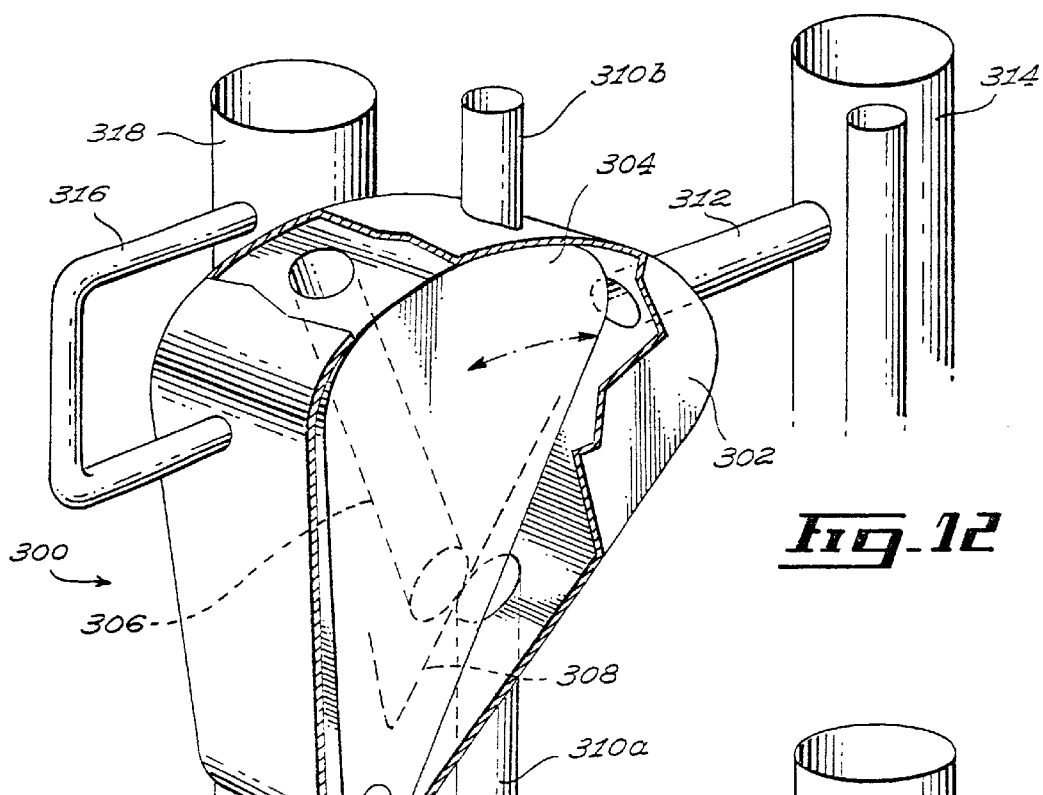

FIG. 12 schematically shows the inline fluid circuit of a fifth embodiment of a valve member 300 according to the invention. In this embodiment, the valve member 300 comprises an inner chamber 302 in which is pivotable an actuator 304 having a single passage 306 therein. In use, when the dental handpiece is in an inoperative condition, actuator 304 is pivotally biased by a coil spring 308 so that the downstream segment 310a of the cooling water conduit communicate through chamber 302 with a first transverse inner channel 312, the latter in turn connected to the discharge conduit 314. Thus, in this position of block actuator 304, the water flows constantly through the water conduits, being dispatched through the discharge conduit 314. When the bur head is activated, a high-pressure air flow enters chamber 302 through a second transverse inner channel 316 and from the bur air conduit 318, to pivotally bias block actuator 304 against the action of spring 308 until the inner passage 306 comes in register with the downstream and upstream segments 310a, 310b of the cooling water conduit Thus, the cooling water is allowed to be fed to the dental handpiece.

Figure 13:
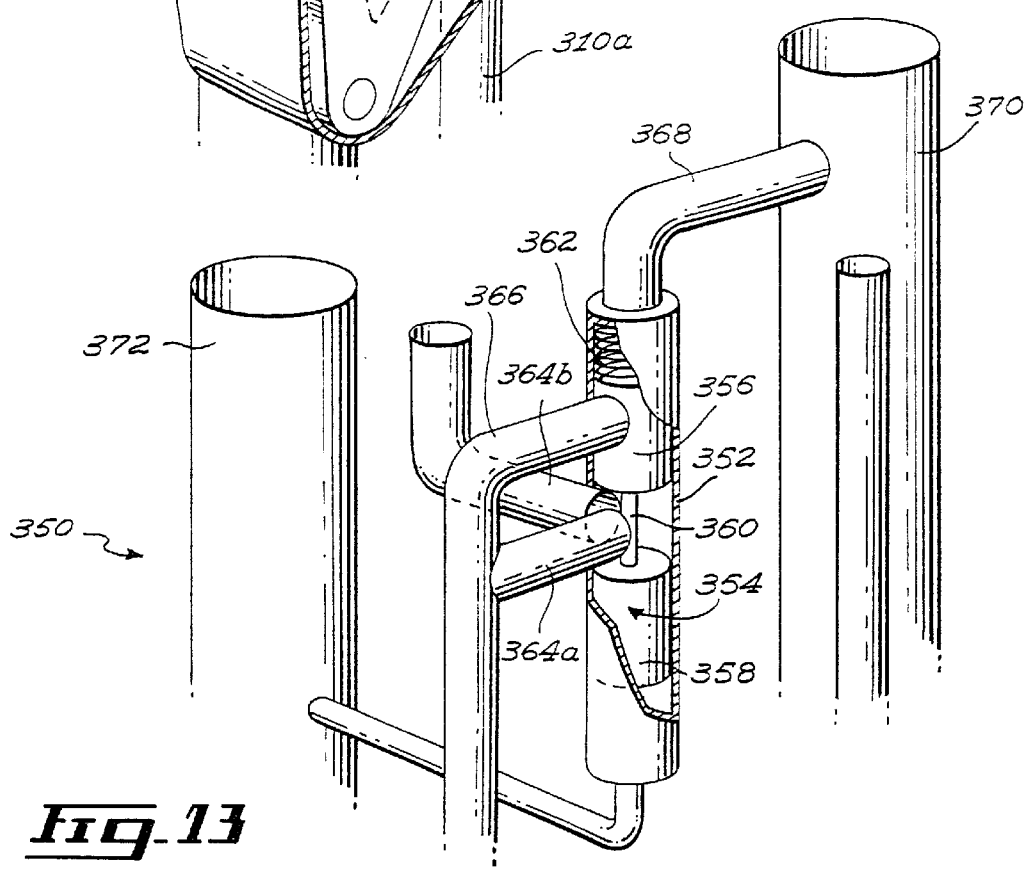

FIG. 13 schematically shows the inline fluid circuit of a sixth embodiment of a valve member 350 according to the invention. In this embodiment, the valve member 350 includes a piston channel 352 in which is slidable a piston 354 having two cylinders 356, 358 coaxially linked by an intermediate spacer rod 360, similar to the piston shown in the embodiment of FIGS. 6–9. Valve member 350 further includes a spring 362 continuously biasing piston 354 in a first limit position, in which piston 354 blocks with its first cylinder 356 the registering segments 364a, 364b of the cooling water pipe. In this first position of piston 354, the cooling water is redirected in a bypass channel 366, through piston channel 352, and into a discharge channel 368 and a discharge conduit 370. However, under a high-pressure air flow running in the high-pressure air conduit 372, piston 354 is biased against the action of spring 362 into a second limit position, in which the first cylinder 356 blocks bypass channel 366, and in which the cooling water is allowed to flow from the first segment 364a to the second segment 364b of the cooling water conduit, to feed the dental handpiece.

Thus, it can be seen that according to the present invention, many different actuator devices, including pistons, can be used to direct the cooling water flow alternately into the discharge conduit or into the dental handpiece, with corresponding conduit configurations being provided accordingly. Any additional modifications to the present invention which have not been illustrated or described herein and which do not deviate from the scope of the present invention, are considered to be included therein.

For example, FIGS. 1–5 show a valve member including several inner transverse channels, namely a piston channel 80, a first inner air channel 82, a second inner water channel 84, and a third inner discharge channel 86. However, it must be understood that the water channel 84, the discharge channel 86 and the portion of the piston channel 80 which link the two former channels, all form a bypass channel which may be identified as a single channel. It could be envisioned to design a valve member having a single bypass channel linking all three of the high-pressure air conduit 70, the water conduit 72 and the discharge conduit 76, to operatively move the piston in the bypass channel responsive to the air pressure in the high-pressure air conduit 70, and responsive to the bias of a coil spring.

Concerning the coil spring, it is understood that any suitable biasing member of known construction, such as an arm made of a resilient material or a blade spring, torsion spring or other biasing device, would also be acceptable. It could furthermore be envisioned that the piston or actuator be manually movable from its first to its second limit position, but this is not the preferred way to carry out the invention.

It is understood that the coupling between the water circulation device of the present invention and the main tubing, and the coupling between the water circulation device and the dental handpiece, have been chosen to correspond to the couplings found on conventional dental handpiece sockets. It must thus be understood that the nozzles or other coupling members described in the present specification and illustrated in the drawings, could be replaced with any other suitable nozzles, coupling member or mounting devices.

I claim:

1. A valve member for operatively linking a dentist cabinet dental handpiece, of the type which selectively requires a water flow and which includes a water inlet nozzle and a discharge outlet nozzle, to a main tubing, of the type having a water tube outlet and a discharge tube inlet, the water tube outlet providing a continuous positive water flow, said valve member comprising:
    a water conduit for operatively fluidingly linking the water tube outlet to the dental handpiece water inlet nozzle, a continuous positive water pressure thus being present in said water conduit for allowing selective water flow out through the dental handpiece;
    a discharge conduit for operatively fluidingly linking the discharge tube inlet to the dental handpiece discharge outlet nozzle, the pressure in said discharge conduit being inferior to the pressure in said water conduit;
    a bypass channel linking said water conduit to said discharge conduit; and
    an actuator, selectively movable in said bypass channel between a first limit position, in which said actuator allows fluid access through said bypass channel from said water conduit to said discharge conduit, and a second limit position, in which said actuator blocks in a fluid-tight fashion said bypass channel for preventing fluid from flowing between said water conduit and said discharge conduit;
        wherein in said first limit position of said actuator, water flowing in said water conduit will be redirected through said bypass channel to be dispatched in said discharge conduit for allowing continuous flow of the water in the tubing to prevent water stagnation, while in said second limit position of said actuator, water flowing in said water conduit will be forced to flow through said valve member and into the dental handpiece.

2. A valve member as defined in claim 1, with the dental handpiece further being of the type having a high-pressure air inlet nozzle and the tubing further being of the type having a high-pressure air tube outlet selectively providing a high-pressure air flow, wherein said valve member further comprises:
    a biasing member, for continuously biasing said actuator towards said first limit position;
    a high-pressure air conduit for operatively fluidingly linking the high-pressure air tube outlet to the dental handpiece water inlet nozzle; and
    an air channel linking said air conduit to said bypass channel, for forcibly biasing said actuator towards said second position, against the action of said biasing member, upon the high-pressure air flow being fed into said high-pressure air conduit; said actuator, in all positions thereof, sealingly blocking said bypass channel to prevent fluid from flowing between said air conduit and both said water conduit and said discharge conduit.

3. A valve member as defined in claim 2, wherein said actuator is a piston slidable in said bypass channel.

4. A valve member as defined in claim 3, wherein said biasing member is a coil spring located in said bypass channel.

5. A valve member as defined in claim 2, in combination with the dental handpiece, said dental handpiece having a head portion requiring in an operative condition thereof a high-pressure air flow fed by a handpiece high-pressure air conduit connected to said air inlet nozzle, and a cooling water flow fed by a handpiece cooling water conduit connected to said water inlet nozzle, said dental handpiece expelling at least a portion of said air flow through a handpiece discharge conduit connected to the handpiece discharge outlet nozzle.

6. A water circulation device for preventing water stagnation in the tubing of a dentist cabinet dental waterline unit, said water circulation device for linking a dental handpiece to the tubing, the tubing of the type having a high-pressure air tube for selectively providing a high-pressure air flow to the dental handpiece, a cooling water tube for providing a continuous water cooling water flow for the dental handpiece, a cooling air tube for providing a cooling air flow for atomizing the cooling water into a cooling water spray, and a discharge tube, in which part of the high-pressure air flow are carried away from the dental handpiece, said water circulation device including a valve member comprising:

a high-pressure air conduit, a cooling air conduit, a cooling water conduit and a discharge conduit, each for operatively fluidingly linking respectively the high-pressure air tube, the cooling water tube, the cooling air tube and the discharge tube to the dental handpiece;

a bypass channel fluidingly linking said cooling water conduit to said discharge conduit;

a piston movable in said bypass channel, between a first unobstructive position in which the water is free to flow from the water conduit into the discharge conduit, and a second obstructive position in which said piston blocks in a fluid-tight fashion said bypass channel, to prevent the water from flowing into the discharge conduit;

a biasing member continuously biasing said piston towards said first limit position; and an air channel linking said bypass channel to said high-pressure air conduit, with said piston blocking said bypass channel between said air channel and both said water and said discharge conduits in all positions of said piston, said piston being forcibly moved towards said second limit position responsive to the presence of a high-pressure air flow in said high-pressure air conduit;

wherein, when no high-pressure air flow runs through said high-pressure air conduit, said piston remains in said first limit position under the bias of said biasing member and water is free to flow through said bypass channel from said water conduit into said discharge conduit, thus not reaching the handpiece, for allowing the water to continuously flow to prevent the water from stagnating in the tubing; and wherein, when a high-pressure air flow runs through said high-pressure air conduit, the high-pressure air flow forces said piston against the action of said biasing member towards said second limit position, thus blocking said bypass channel and allowing the water to flow out of said cooling water conduit for feeding the handpiece.

7. A water circulation device as defined in claim 6, wherein said actuator is a piston slidable in said bypass channel.

8. A water circulation device as defined in claim 7, wherein said bypass channel comprises a piston channel segment, in which said piston is slidable between said first and second limit positions, a water channel segment linking said water conduit to said piston channel segment, and a discharge channel segment linking said discharge conduit to said piston channel segment, with said water channel segment being located intermediate said discharge channel segment and said air channel, with said piston being located in said first limit position intermediate said air channel and said water and discharge channel segment, and with said piston blocking said water channel segment in said second limit position.

9. A water circulation device as defined in claim 8, wherein at least one channel among said piston channel segment, said water channel segment, said discharge channel segment and said air channel is pierced from the outer periphery of said valve member inwardly therein thus forming at least one corresponding channel segment opening at the periphery of said valve member, said at least one channel segment opening being blocked with a sealing plug.

10. A water circulation device as defined in claim 9, further comprising a sealing ring located around said valve member and holding each said at least one channel segment opening.

11. A water circulation device as defined in claim 10, further comprising a hollow connector sleeve carrying said sleeve member, said connector sleeve having a first end portion for complementary engagement to said dental handpiece, and a second end portion for complementary engagement to said tubing.

12. A water circulation device as defined in claim 8, wherein said biasing member is a coil spring located in said piston channel segment.

13. A process of making a water circulation device as defined in claim 10, comprising the steps of:

a) moulding a valve member blank;

b) longitudinally piercing in said valve member blank said high-pressure air conduit, said cooling water conduit, said cooling air conduit and said discharge conduit;

c) transversely piercing in said valve member blank said air piston channel segment, said air channel, said water channel segment and said discharge channel segment, thus creating at least one transverse opening in said blank;

d) installing sealing plugs in each one of said at least one openings; and e) forcing in a friction-fit engagement said sealing ring about said valve member for holding said plugs.

* * * * *